United States Patent
Kerrod et al.

[11] Patent Number: 5,843,700
[45] Date of Patent: Dec. 1, 1998

[54] TISSUE PROCESSING APPARATUS AND METHOD

[75] Inventors: Ian Michael Kerrod, Deeside; George Alan Walton, Tarporley, both of United Kingdom

[73] Assignee: Shandon Scientific Limited, Runcorn, United Kingdom

[21] Appl. No.: 15,262

[22] Filed: Jan. 29, 1998

[30] Foreign Application Priority Data

Jan. 30, 1997 [GB] United Kingdom ............... 9701930

[51] Int. Cl.⁶ ................................................ C12Q 1/08
[52] U.S. Cl. ............... 435/40.5; 435/40.52; 435/30.71; 422/102; 422/104; 425/117; 118/429; 118/500; 220/307; 220/339
[58] Field of Search ............................. 435/284.1, 288.4, 435/307.1, 30, 40.5, 40.32; 422/102, 104; 425/117; 118/429, 500; 220/307, 339

[56] References Cited

U.S. PATENT DOCUMENTS

| | | | |
|---|---|---|---|
| 4,801,553 | 1/1989 | Owen et al. | 436/174 |
| 5,543,114 | 8/1996 | Dudek | 422/102 |
| 5,665,398 | 9/1997 | McCormick | 425/117 |

*Primary Examiner*—David A. Redding
*Attorney, Agent, or Firm*—Fulwider Patton Lee & Utecht, LLP

[57] ABSTRACT

Apparatus for processing tissue samples for histological examination comprises a cassette defining a chamber to receive a tissue specimen and having an opening to allow processing fluids to enter and leave the chamber and to allow, eventually, molten wax to enter the chamber for embedding the tissue sample. The apparatus incorporates a temperature-sensitive valve mechanism for closing said opening once the cassette, with the tissue specimen therein, has been immersed in a container of hot molten wax, so that the wax can be retained in the cassette, around the specimen, when the cassette is withdrawn from the molten wax container, until the wax around the specimen has solidified. The temperature sensitive valve mechanism may comprise a shape-memory element.

6 Claims, 1 Drawing Sheet

5,843,700

TISSUE PROCESSING APPARATUS AND METHOD

THIS INVENTION relates to apparatus for use in preparation of tissues for histological examination and to a method of preparing tissues for histological examination.

It is known to prepare tissue samples for histological examination by treating such samples in a series of processing fluids and finally soaking the samples in molten paraffin wax which is allowed to solidify to form a support for the tissue, allowing the tissue to be mounted conveniently in a microtome for cutting the sample into thin sections suitable for microscopic examination.

It is furthermore known to effect such tissue processing automatically by means of a dedicated processing machine. Typically, processing of tissue samples using such automatic processing machines involving placing each tissue sample in a respective perforated container or cassette which is in turn placed with other similar containers or cassettes, containing respective samples, in the processing machine, which treats each sample, contained in its respective cassette, in each of a plurality of treatment liquids in succession, after which each specimen is removed from its cassette and placed manually in the required orientation for sectioning in a mould part containing a small volume of molten wax, which wax is then cooled to retain the specimen. The body of the original cassette is then placed on the top of the mould part and molten wax is added to completely fill the mould part and permeate the cassette body thereon, thereby to attach the specimen to the cassette body. After the wax has solidified the mould is removed and the specimen remains attached to the cassette body, which is then used for mounting the specimen in a microtome.

It is an object of the present invention, in one aspect, to provide apparatus by means of which a specimen may be processed and subsequently embedded in wax in one automated operation without requiring human intervention between the processing stages and the wax embedding stage.

According to the invention, there is provided, in one aspect, tissue processing apparatus including a cassette defining a chamber to receive a tissue specimen for processing, the cassette having at least one opening to allow processing fluids to enter and exit from said chamber and means for closing said opening automatically to retain, within said chamber, molten wax or an analogous tissue supporting medium, introduced into said chamber in a final processing stage, until solidification of such wax or analogous medium.

According to another aspect of the invention, there is provided a tissue processing cassette defining a specimen chamber to receive a tissue specimen for processing, the cassette having at least one opening to allow processing fluids to enter and exit from said chamber, and further having a gas chamber in communication with said specimen chamber and adapted, in at least one orientation of the cassette in a surrounding liquid, to hold captive a body of gas which can expand or contract, with accompanying exit of such liquid from the gas chamber or entry of such liquid into the gas chamber, in response to reduction or increase, respectively, of the pressure of said surrounding liquid.

According to a still further aspect of the invention, there is provided a method of treating a tissue specimen for histological examination, comprising providing a tissue processing cassette in accordance with the firstnoted aspect of the invention, mounting the tissue specimen in a predetermined orientation in said chamber, immersing said cassette, with said specimen therein, successively in each of a plurality of treatment liquids including, finally, molten wax or an analogous tissue supporting medium, closing said opening to retain such molten wax or analogous medium within said chamber around the specimen, withdrawing the cassette from the molten wax or analogous medium in which it is immersed and allowing the wax or analogous medium within the cassette to solidify, and subsequently extracting from the cassette or from a part thereof the composite body comprising the tissue specimen and surrounding hardened wax or the like and mounting said body in a predetermined orientation in a microtome.

BRIEF DESCRIPTION OF DRAWINGS

An embodiment of the invention is described below by way of example with reference to the accompanying drawings, in which:

Referring to FIGS. 1 and 2, the tissue processing cassette shown comprises a plastics body 2, (herein also referred to as a mould), in the form of a container providing an open-topped specimen chamber 5 closed by a removable lid or cover 1, which may also be of plastics and which, in manner known per se, also forms a specimen mounting plate by means of which, after the tissue treatment and wax mounting stages, the block of wax which contains the treated tissue specimen and which adheres to the mounting plate, can be mounted on a complementary part of a microtome, for sectioning the wax-embedded specimen. In the arrangement illustrated in FIG. 1, the lid 1 and the upper rim of the mould 2 are so formed that the lid 1 is a snap-fit within the upper rim of mould 2 and can be removed therefrom after flexing the upper edge of the containing by applying pressure to a tab 2a formed at the upper edge of mould 2 at one end thereof. The cover 1 is formed with apertures 1a therethrough. The mould 2 has a flat base 2b which formed with apertures 2c therethrough. A flat, plate-like portion 4a of a valve member 4 is in sealing engagement with the underside of base 2b and the valve member 4 is slidable parallel with the planes of the base 2b and plate-like portion 4a in such a way as to maintain plate-like portion 4a in sealing engagement with the base 2b. To this end, the plate-like portion 4a may, as illustrated, be formed with elongate guide slots 4b through which pass retaining pins integral with the base 2b and which have enlarged heads extending over the lower surface of plate-like portion 4a (and formed, for example, by a "rivetting" or upsetting operation).

Figure 1:
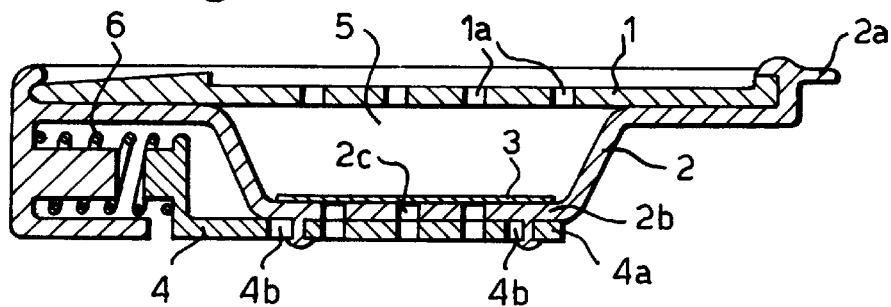
FIG. 1 is a view in longitudinal section of a tissue processing cassette in accordance with the present invention.

The plate-like portion 4a of valve member 4 has apertures therethrough which, in the position shown in FIG. 1 of the member 4 relative to the mould 2, are in register with respective apertures 2c in mould 2.

A shape memory alloy spring 6, for example of titanium-nickel alloy, acting between the mould 2 and one end of the valve member 4 serves to displace the member 4 to a position sealing off the openings 2c when the temperature of spring 6 rises above a predetermined value, for example 50° C. The spring 6, (or alternatively a catch mechanism, not shown), thereafter retains the member 4 in its position sealing off the openings 2c when the temperature subsequently falls below that predetermined value. The spring 6 may be a helical coil spring, a leaf spring or a spring of some other form. The spring can be restored to its condition allowing the openings 2c to remain open by compressing it manually whilst it is substantially below said predetermined temperature. Alternatively a further, bias spring, (not shown) can be used to compress spring 6 and move member 4 to its position opening the openings 2c when the temperature is substantially below said predetermined temperature.

Figure 2:
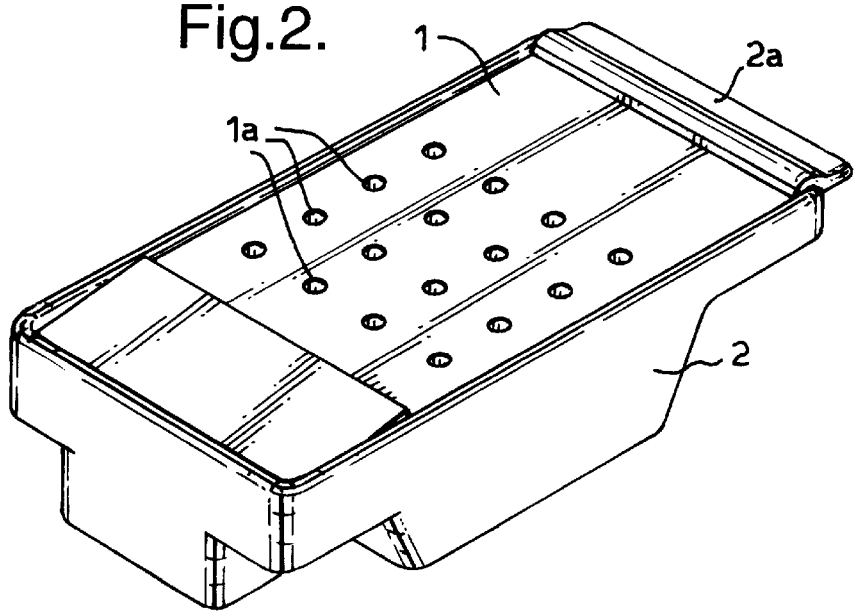
FIG. 2 is a perspective view of the processing cassette of FIG. 1.

In use of the cassette of FIGS. 1 and 2, a tissue specimen for processing is orientated in the cassette by a suitably qualified technician and retained in the desired orientation by some suitable mounting means such as the mounting gel referred to below. The lid 1, which is also destined to form a mounting plate whereby the specimen may be mounted in a microtome, is marked with an identifying code for the specimen. This lid or mounting plate remains with the specimen and is attached thereto at the embedding stage as explained below.

The cassette containing the tissue specimen is placed in a conventional tissue processing machine which processes the specimen by treating it with a series of processing fluids before immersing the cassette, with the tissue specimen therein, in molten wax. All of the processing stages including the wax stages take place at a temperature below that required to actuate the SMA spring 6, for example 50° C. During the final wax cycle the temperature of the wax is raised above the point at which the memory effect of the spring causes it to extend, for example to 60° C., which causes the spring to move valve 4 to close the openings 2c in the base of mould 2. The cassette then effectively becomes a liquid-tight container that will retain the molten wax inside if either the wax chamber in the processing machine is drained or the cassette is removed from the molten wax bath. (It will be understood that the orientation of the cassette during processing is intended to be that shown in FIGS. 1 and 2, i.e. with the cover 1 uppermost and the plate 4 lowermost). The molten wax thus retained in the cassette, around the specimen, solidifies in the cassette as the temperature falls and, because the wax extends through the holes 1a in plate 1, becomes firmly attached to lid 1 and at the same time firmly holds the tissue sample. The mould portion 2 of the cassette can be removed once the wax has solidified, leaving the wax-embedded specimen attached to the plate 1 which is used to mount the specimen in a microtome, in manner known per se, ready for cutting into sections for mounting on slides for microscopic examination.

As indicated above, in the processing method of the present invention, it is necessary for the tissue specimen to be placed and retained in the desired orientation relative to the cassette before processing commences since wax embedding automatically directly follows the preceding automatic processing stages.

Various techniques can be used for maintaining the specimen in its desired orientation. One technique currently preferred is to use a known two-part gel system such as that available from Life Sciences International (Europe) Limited under the name Shandon Cytoblock Gel. This gel system includes a first liquid component which when contacted by a second liquid composition, (which acts as a "catalyst" or "hardener"), sets into a gel.

Figure 3:
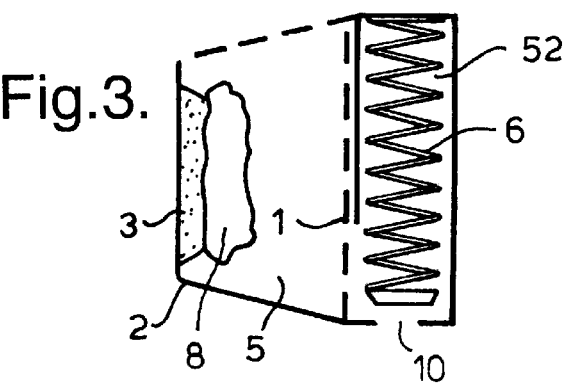
FIG. 3 is a schematic cross-sectional view of a variant processing cassette in accordance with the invention.

In use of such a gel system to mount a specimen in the cassette, a layer of the first liquid component is applied to part of the inner surface of mould part 2 of the cassette. The specimen is then placed in the mould part of the cassette in contact with the layer of said first liquid component and is held in its desired orientation, in contact with said layer, while the second liquid component is applied to the layer. The gel rapidly solidifies and the specimen is thereby held in the desired orientation during subsequent processing. The first and second liquid components of the gel system could for example be applied by dispensing from a bottle with a fine nozzle, from a syringe or in some other way. The second liquid component could, if desired, be applied by spraying it onto said layer of the first component on the base of mould 2. The gel processes in a similar manner to the tissue and does not affect the processing of the tissue. It is not affected by the processing reagents, it does not stain and it does not affect tissue sectioning. For ease of illustration in FIG. 1, the layer of gel, indicated at 3, has been illustrated as extending over the base in which the apertures 2c are formed. It will be understood, however, that in order to avoid blocking the apertures 2c by the gel, it would be necessary to apply the gel to some part of the interior of mould 2 other than that in which apertures 2c are formed, or, if the gel is applied to the base of mould 2, to have the openings 2c and the valve plate cooperating therewith, in some other part of the mould, for example, as indicated in FIG. 3.

The mould portion 2 of the cassette is then removed to leave the tissue specimen attached to plate or cover 1 which has the specimen identifier marked on it and is also used for mounting it in a microtome for sectioning.

It will be appreciated that any of a wide variety of valve mechanisms may be utilised instead of that described with reference to FIG. 1. Furthermore, whilst a shape memory alloy spring has been described as a means of operating the valve, other means may be adopted, which may or may not be temperature dependent, such as bistable spring elements of the kind used in thermostatic switches.

The provision of a valve mechanism for retention of wax within the cassette places constraints upon the total flow cross-section which may be made available for the flow of processing reagents into and out of the cassette to treat the specimen, so that this flow cross-section may have to be significantly smaller than in a conventional cassette where the area of the holes in the cassette walls may comprise a very large proportion of the total area of the walls of the cassette. This reduction in the flow cross-section available for the flow of reagents into and out of the cassette may have the effect of increasing the processing time required. In order to counteract this effect, a mechanism may be provided to improve fluid transfer through the cassette. This can be achieved by incorporating a gas chamber (air chamber) within the cassette as illustrated in FIG. 3, which gas chamber is in communication with the specimen chamber in the cassette and is adapted, in the normal orientation of the cassette in the automatic processing apparatus, to hold captive a body of gas which contract or expand by the entry of liquid into the gas chamber from a specimen chamber, or the exit of such liquid from the gas chamber to the specimen chamber. It is normal practice to use alternating pressure and vacuum in automatic processing machines to assist fluid penetration of the specimens. With an integral gas chamber the pressure and vacuum cycles cause the gas volume of the gas chamber to contract and expand. This in turn has the effect of increasing fluid flow through the cassette by the resulting pumping action.

FIG. 3 illustrates such a gas chamber arrangement. The cassette illustrated in FIG. 3 may comprise a body or mould part 2 again providing a specimen chamber 5 again closed by a perforated closure plate which is again releasably engaged with mould 2 and is again adapted to serve as a specimen mounting plate for retaining a wax-supported specimen for mounting in a microtome.

The cassette of FIG. 3, however, is adapted to be mounted in the automatic processing machine in the orientation illustrated, that is to say so that the closure 1 forms a vertical side wall of the cassette, rather than the top thereof and so that one wall of mould 2, formed with perforations as illustrated, lies uppermost. In the arrangement shown in FIG. 3, the gel 3 secures the specimen (8) to the wall of the cassette which forms the side wall directly opposing the closure 1. The wall of the cassette which lies uppermost and forms the top of chamber 5 in the orientation illustrated in FIG. 3 may be perforated by a plurality of openings as illustrated in FIG. 3.

The mould 2 in FIG. 3 includes a formation providing a gas (air) chamber 52 which is in communication with the specimen chamber 5 adjacent the lower end (as viewed in FIG. 3) of the gas chamber. As illustrated in FIG. 3, the gas chamber 52 may, if desired, form a housing for a helical shape memory alloy spring 6 which in this embodiment serves, when raised above its predetermined critical temperature, to urge a valve member into engagement with a drainage hole 10 at the lower end (as viewed in FIG. 3) of the cassette, and which provides the only exit for liquid to drain under gravity from the specimen chamber. The upper portion of chamber 52 is of course closed so that the air therein is trapped by the liquid within the cassettes. It will be understood that, in order to ensure that, during pressure and vacuum cycling, the treatment fluid does not simply short-circuit the treatment chamber 5 and pass directly into and from the gas chamber 52, it is necessary to ensure that the effective flow cross-section of the drainage hole 10 is small in relation to the flow cross-section of the other apertures in mould part 2 or closure 1, or to position the drainage hole 10 physically remote from the gas chamber 52 with an appropriate actuating arrangement extending between the spring 6 and the valve member cooperating with the drainage hole.

The location of the shape memory alloy spring 6 within the gas chamber in the arrangement of FIG. 3 is advantageous as the helical spring has a large envelope whilst having a relatively small material volume.

We claim:

1. Tissue processing apparatus including a cassette defining a chamber to receive a tissue specimen for processing, the cassette having at least one opening to allow processing fluids to enter and exit from said chamber and means for closing said opening automatically to retain within said chamber molten wax or an analogous tissue supporting medium introduced into said chamber in a final processing stage until solidification of such wax or analogous medium.

2. A tissue processing apparatus according to claim 1 wherein said means for closing said opening automatically is responsive to temperature.

3. Tissue processing apparatus according to claim 2 wherein said means for closing said opening automatically comprises a temperature-sensitive shape memory element.

4. Apparatus according to any of claims 1 to 3 wherein said cassette includes a wall having said opening therein and said means for closing said opening automatically includes a plate sealingly engaging said wall and slidable along said wall between a first position and a second position, said plate having an aperture therein which in said first position is in register with said opening and which in said second position is out of register with said opening whereby the plate closes said opening in said wall, and means for moving said plate automatically from said first to said second position.

5. A tissue processing cassette defining a specimen chamber to receive a tissue specimen for processing, the cassette having at least one opening to allow processing fluids to enter and exit from said chamber, and further having a gas chamber in communication with said specimen chamber and adapted, in at least one orientation of the cassette in a surrounding liquid to hold captive a body of gas which can contract or expand, by the entry of such liquid into the gas chamber or the exit of such liquid from the gas chamber, in response to increase or reduction, respectively, of the pressure of said surrounding liquid.

6. A method of treating a tissue specimen for histological examination, comprising providing a tissue processing cassette in accordance with claim 1, mounting the tissue specimen in a predetermined orientation in said chamber, immersing said cassette, with said specimen therein, successively in each of a plurality of treatment liquids including, finally molten wax or an analogous tissue supporting medium, closing said opening to retain such molten wax or analogous medium within said chamber around the specimen, withdrawing the cassette from the molten wax or analogous medium in which it is immersed and allowing the wax or analogous medium within the cassette to solidify, and subsequently extracting from the cassette the composite body comprising the tissue specimen and surrounding hardened wax or the like and mounting said body in a predetermined orientation in a microtome.

* * * * *